United States Patent [19]

Shaw et al.

[11] 4,307,247

[45] Dec. 22, 1981

[54] PROCESS FOR THE PRODUCTION OF UNSATURATED ACIDS AND ESTERS

[75] Inventors: Wilfrid G. Shaw, Lyndhurst; James E. Rinz, Bedford; Christos Paparizos, Willowick, all of Ohio

[73] Assignee: Standard Oil Company, Cleveland, Ohio

[21] Appl. No.: 184,591

[22] Filed: Sep. 5, 1980

[51] Int. Cl.³ .................. C07C 51/377; C07C 57/05; C07C 67/317; C07C 69/54
[52] U.S. Cl. .................. 562/599; 252/435; 252/437; 560/214; 568/397
[58] Field of Search .................. 560/214; 562/599; 260/405.5; 252/437, 435

[56] References Cited

U.S. PATENT DOCUMENTS 3,917,673 11/1975 Watkins .................. 560/599
4,061,673 12/1977 Onoda et al. .................. 560/599
4,081,465 3/1978 Gruber et al. .................. 560/599
4,232,174 11/1980 Statz et al. .................. 560/599

FOREIGN PATENT DOCUMENTS 48-19614 6/1973 Japan .................. 562/599

Primary Examiner—Vivian Garner
Attorney, Agent, or Firm—Gary R. Plotecher; Herbert D. Knudsen; Larry W. Evans

[57] ABSTRACT

Saturated, lower aliphatic acids and esters are oxydehydrogenated to the corresponding unsaturated acids and esters by use of a catalyst of the empirical formula:

$$Mo_{12}P_{0.1-3}Bi_{0.01-2}Mo_{0.1-3}Cu_{0.01-2}V_{0.01-3}X_aM'_bO_c \quad (I)$$

where
M is at least one of K, Rb and Cs;
X is at least one of Ba, Zn, Ga, Cd, Ti, when $a>0$;
M' is at least one of Ca, Mg, Ta, Zr, Ce, Ni, Co, Cr, Fe and Tl when $b>0$;
a is a number of 0 to about 2;
b is a number of 0 to about 2; and
c is a number that satisfies the valence requirements of the other elements present.

12 Claims, No Drawings

PROCESS FOR THE PRODUCTION OF UNSATURATED ACIDS AND ESTERS

BACKGROUND OF THE INVENTION

1. Field of the Invention

This invention relates to catalysis. In one aspect, the invention relates to the catalytic oxydehydrogenation of saturated, lower aliphatic acids and esters to the corresponding unsaturated acids and esters while in another aspect, the invention relates to the manufacture of methacrylic acid by the oxydehydrogenation of isobutyric acid with a heteropolyacid, bismuth-containing catalyst.

2. Description of the Prior Art

U.S. Pat. No. 4,061,673 teaches the manufacture of methacrylic acid by the oxidative dehydrogenation of isobutyric acid using a heteropolyacid consisting of molybdenum, tungsten, vanadium, phosphorus and oxygen. The catalyst is supported on a carrier having a silicon dioxide content of at least 70% and a water absorbability of at least 60%.

U.S. Pat. No. 3,917,673 teaches the synthesis of unsaturated, lower aliphatic acids and esters by the catalytic oxidative dehydrogenation of the corresponding saturated acids and esters. The catalyst is the calcined residue of a mixture of bismuth oxynitrate, iron phosphate and lead phosphate.

Other processes and catalysts are known for the oxidative dehydrogenation of isobutyric acid and similar materials to methacrylic acid and similar products. Representative of these include DT No. 2,438,464, BE No. 848,300 and JAP Nos. 3,082,720, 2,105,112, 2,105,113, 1,118,718, 2,039,622 and 2,031,018.

SUMMARY OF THE INVENTION

According to this invention, saturated, lower aliphatic acids and esters are oxydehydrogenated to the corresponding unsaturated acids and esters by use of the catalyst of the empirical formula:

$$Mo_{12}P_{0.1-3}Bi_{0.01-2}M_{0.1-3}Cu_{0.01-2}V_{0.01-3}X_aM'_bO_c \qquad (I)$$

where
M is at least one of K, Rb and Cs;
X is at least one of Ba, Zn, Ga, Cd, Ti, when a>0;
M' is at least one of Ca, Mg, Ta, Zr, Ce, Ni, Co, Cr, Fe and Tl when b>0;
a is a number of 0 to about 2;
b is a number of 0 to about 2; and
c is a number that satisfies the valence requirements of the other elements present, Use of these catalysts gives good per pass conversions of the saturated acids and esters and good selectivity to the unsaturated products.

DETAILED DESCRIPTION OF THE INVENTION

The saturated, lower aliphatic acids and esters of this invention are of the empirical formula:

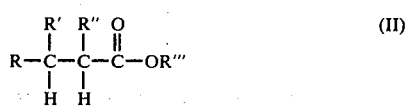

(II)

where R-R''' are independently hydrogen or a $C_1$-$C_4$ alkyl radical. Preferred starting materials are the acids (R''' is hydrogen) while more preferred starting materials are acids where R and R' are hydrogen. Isobutyric acid (R, R' and R''' are each hydrogen and R'' is methyl) is especially preferred. These lower, saturated acids and esters can contain inert substituents, i.e., substituents that are essentially nonreactive with the process reactants, catalysts and products at process conditions, but are preferably free of substituents.

Molecular oxygen can be used in either a relatively pure form or diluted by one or more carrier gases. For reasons of economy and convenience, the molecular oxygen is usually introduced as air.

As is evident from formula I, the catalytic composition of this invention is at least a seven element material, i.e., a material containing molybdenum, phosphorus, bismuth, alkali metal (M), copper, vanadium and oxygen all in designated proportional amounts. Preferably, the subscript value of phosphorus in formula I is about 0.8 to 1.5, of bismuth about 0.15 to 1, of alkali metal (M) about 0.15 to 2, of copper about 0.2 to 0.8 and of vanadium about 0.2 to 0.8.

Preferred catalysts of this invention are those where a is greater than 0, and preferably a number of about 0.01-2. These preferred catalysts demonstrate unusually good methacrylic acid selectivities, particularly those where X is zinc, cadmium, titanium or barium. These preferred catalysts can be further enhanced at least in terms of activity and, in some cases, thermal stability, by the addition of yet another component, here designated M'. When component M' is present (b is greater than 0), it is generally as calcium, magnesium, thallium, tantalum or zirconium.

As is taught by formula I, certain of the components can be combinations of two or more elements, e.g., X can be a combination of barium and zinc. In such instances, the subscript value represents the sum of the elements (e.g. for X, the sum of barium and zinc is equal to a which is less than or equal to about two). Generally M, X, and M' each represent but a single element.

Particularly preferred catalytic compositions are eight element or component (including oxygen) catalysts where M is rubidium or potassium, X is zinc or cadmium, a is about 0.05 to about 2 and b is 0.

The exact structure or element arrangement of these catalysts is not known but the metal and phosphorus components are present in the form of their oxides, acids, or oxyacid complexes. However, the compositions of formula I are known not to be a mere physical mixture of their components but rather unique heteropolyacids or derivatives where the individual components are chemically and/or physically bonded to one another.

The catalytic compositions of this invention can be used either in the 100% active form or in a diluted form, i.e. supported or unsupported. Suitable support materials include silica, titania, alumina, zirconia, silicon carbide, boron, various phosphate, etc., with low surface area (about 1 m²/g) alumina a preferred support material. If a support is used, the catalytic composition is generally present in an amount of at least 20 weight percent, based on the combined weight of the support and the catalytic composition, and preferably in an amount of at least about 30 weight percent.

The catalytic compositions of this invention can be prepared by any one of a number of different methods, the particular method employed being a matter of convenience. Typically, the catalysts are prepared by mixing the appropriate catalyst ingredients in the proper proportions in an aqueous mixture, drying the resulting aqueous slurry with or without a reducing agent, and calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, acetates or other salts of the particular metals or elements added, and particularly preferred is the use of water soluble salts of the metal components. If a support is used, the material comprising the support may be incorporated into the catalyst along with the other ingredients or the catalyst composition may be coated and/or impregnated onto or into a core. After the catalyst ingredients have been combined to form an aqueous slurry, the slurry is taken to dryness and the dried solid obtained is heated in the presence of air, nitrogen, nitric oxide or a mixture of any two or more of these gases at temperatures between about 200° and 400° C. This calcination can take place outside the catalytic reactor or an in situ activation can be utilized. Other methods of preparation are known in the art.

The process of this invention is conducted in the vapor phase. The vaporous, saturated starting material is contacted with the solid catalyst in the presence of molecular oxygen. Any temperature at which the starting material is vaporous can be employed but preferably the temperature is between about 270° and 355° C. Likewise, any pressure at which the starting material is vaporous can be employed and these pressures range from subatmospheric to superatmospheric. Typically, autogenous pressure is employed. The molar ratio of oxygen to saturated acid or ester can also vary widely with typical molar ratios ranging from about 0.5 to about 3 and preferably from about 0.7 to about 2. As indicated earlier, the feed mixture (acid or ester plus oxygen) can be diluted with a carrier gas, such as nitrogen, water vapor, carbon dioxide, helium, argon or their various mixtures. Sufficient catalyst is employed to insure adequate opportunity for the reaction feed to contact the catalyst surface. Contact time can range from a fraction of a second to several hours or more with a preferred contact time ranging from about 0.1 sec to about 10 sec.

The products of this invention are of the empirical formula:

 (III)

where R-R''' are as defined for formula II. These products have a wide range of utility particularly in the manufacture films, plastic sheets and paints.

The following example is illustrative of a specific embodiment of this invention.

SPECIFIC EMBODIMENTS

Catalyst preparation

The catalyst was prepared by dissolving, with stirring, ammonium heptamolybdate in distilled water and heating the resulting solution to 30°–35° C. While continuously stirring the solution and maintaining the temperature, rubidium hydroxide was added followed by barium hydroxide. After 15 min., copper acetate and ammonium metavanadate solutions were added followed by addition of a bismuth trichloride/hydrochloric acid solution. The resulting slurry was then heated to about 70° C. for two hours. Phosphoric acid (H$_3$PO$_4$) was the last material added after which stirring and heating was continued for 30 min and the pH of the slurry was adjusted to 5.6. The mixture was then evaporated into a thick paste and catalyst precursor dried in an oven at 110°–120° C. The resulting powder was then coated onto ⅛ inch Alundum ® spheres (alumina supports) so that the powder coating (i.e., the catalyst) constituted about 35 weight percent of the coated spheres. The catalyst composition had the empirical formula:

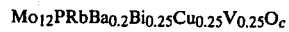

Process Procedure and Conditions

The reaction was conducted in a 20 cc downward-flow, fixed-bed reactor. After the catalyst was introduced into the reactor, it was exposed to one hour of air flow (no feed) at 370° C. followed by about two hours at the reaction temperature of 326° C. with air flow plus feed to equilibrate the catalyst. After the equilibrium period, a 20 min run was made. The VVH (volume of isobutyric acid per volume of catalyst per hour) was about 51.6, the air/isobutyric acid mole ratio was about 4.6 and the water/isobutyric acid mole ratio was about 25.3. The off-gas rate was measured with a soap-film meter and the off-gas composition was determined at the end of the reaction with the aid of a Perkin-Elmer 154 gas chromatograph. At the end of the reaction, the entire scrubber liquid was diluted with distilled water to about 200 g. A weighed amount of methanol was used as an internal standard in a 20 g aliquot of the dilute solution. A one microliter sample was then analyzed in a Hewlett-Packard 5710A gas chromatograph fitted with a flame ionization detector and a SB 1200 column. The splits between methacrylic, acrylic and acetic acid were determined from the gas chromatographic analysis.

The reactor effluent was analyzed as 91.1% converted isobutyric acid with a yield of 61.3% methacrylic acid and 12.2% acetone.

Although this invention is described by the above example, this example is for the purpose of illustration only and it is understood that variations and modifications can be made by one skilled in the art without departing from the spirit and scope of the invention.

The claimed invention is:

1. A vapor-phase process for the production of a compound of the formula

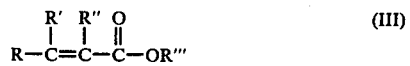 (III)

the process comprising contacting in the presence of molecular oxygen a compound of the formula

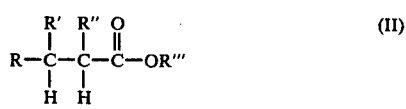 (II)

where R-R''' are independently hydrogen or a C$_1$-C$_4$ alkyl radical, with a catalytic amount of a catalyst of the formula $$Mo_{12}P_{0.1-3}Bi_{0.01-2}M_{0.1-3}Cu_{0.01-2}V_{0.01-3}X_aM'_bO_c \qquad (I)$$

where

M is at least one of K, Rb and Cs;

X is at least one of Ba, Zn, Ga, Cd and Ti when $a>0$;

M' is at least one of Ca, Mg, Ta, Zr, Ce, Ni, Co, Cr, Fe and Tl when $b>0$;

a is a number of 0 to about 2;

b is a number of 0 to about 2; and c is a number that satisfies the valence requirements of the other elements present.

2. The process of claim 1 where $a>0$.

3. The process of claim 2 where M is K or Rb.

4. The process of claim 3 where X is Ba, Zn, Cd or Ti.

5. The process of claim 4 where $b>0$.

6. The process of claim 5 where M' is Ca, Mg, Tl, Ta or Zr.

7. The process of claim 4 where b is 0.

8. The process of claim 7 where the subscript value of P in formula I is a number of about 0.8 to about 1.5, of Bi a number of about 0.15 to 1, of M a number of about 0.15 to 2, of Cu a number of about 0.2 to 0.8 and of V a number of about 0.2 to 0.8.

9. The process of claim 8 where the catalyst is unsupported.

10. The process of claim 8 where the catalyst is diluted with a support.

11. The process of claim 10 where the support is a low surface area alumina.

12. The process of claim 10 where the compound of formula II is isobutyric acid.

* * * * *